US006932940B2

(12) United States Patent
Amirkhanian

(10) Patent No.: US 6,932,940 B2
(45) Date of Patent: Aug. 23, 2005

(54) OPTICAL DETECTION IN BIO-SEPARATION DEVICE USING AXIAL RADIATION INPUT

(75) Inventor: Varouj Amirkhanian, La Crescenta, CA (US)

(73) Assignee: Biocal Technology, Inc., Irvine, CA (US)

( * ) Notice: Subject to any disclaimer, the term of this patent is extended or adjusted under 35 U.S.C. 154(b) by 0 days.

(21) Appl. No.: 09/887,871

(22) Filed: Jun. 22, 2001

(65) Prior Publication Data

US 2002/0197735 A1 Dec. 26, 2002

(51) Int. Cl.$^7$ .............................................. G01M 21/64
(52) U.S. Cl. ............................. 422/82.07; 422/82.06; 435/288.6; 435/288.7; 436/517; 436/164; 204/451; 204/452
(58) Field of Search .............................. 204/450, 451, 204/452, 601; 356/73.1, 317, 318, 413, 417, 344; 436/164, 172, 517; 435/288.6, 288.7, 808; 422/57, 82.06, 82.07, 82.08; 250/458.1, 459.1, 461.1, 461.2

(56) References Cited

U.S. PATENT DOCUMENTS

| | | | | |
|---|---|---|---|---|
| 4,792,689 A | * | 12/1988 | Peterson ............... | 250/458.1 |
| 5,062,942 A | | 11/1991 | Kambara et al. | |
| 5,198,091 A | | 3/1993 | Burolla et al. | |

(Continued)

FOREIGN PATENT DOCUMENTS

| EP | 0386925 | 9/1990 |
|---|---|---|
| EP | 0704699 | 4/1996 |

OTHER PUBLICATIONS

Taylor et al, Axial–Beam Laser–Excited Fluorescence Detection in Capillary Electrophoresis, Anal. Chem. 1992, vol. 64, 1741–1744.*
Yeung et al, Multiplexed Fluorescence Detector for Capillary Electrophoresis Using Axial Optical Fiber Illumination, Anal. Chem. 1993. vol. 65, 956–960.*
Simultaneous Monitoring of DNA Fragments Separated by Electrophoresis in a Multiplexed Array of 100 Capillaries.
DNA Analysis Tools Shrink.
An Integrated Nanoliter DNA Analysis Device.
DNA Sequencing Using Capillary Array Electrophoresis.
Three DNA Sequencing Methods Using Capillary Gel Electrophoresis and Laser–Induced Fluorescence.
DNA Sequencing by Multiple Capillaries that Form a Waveguide.

(Continued)

*Primary Examiner*—Long Le
*Assistant Examiner*—Gary W. Counts
(74) *Attorney, Agent, or Firm*—Liu & Liu

(57) ABSTRACT

In a bio-separation system, incident radiation (e.g., from a laser or LED source) for detection of separated analytes is directed at the detection zone axially along the separation medium, instead of through the boundary walls of the detection zone. In one embodiment, incident radiation at one or more wavelengths is directed via at least one optic fiber that extends axially along the separation medium to the proximity of the detection zone. Emitted radiation from the detection zone passes through the boundary walls about the detection zone for off-column detection, and/or is directed axially along the separation medium for on-column detection. In another aspect of the present invention, the detection zone is located at a widened zone along the separation channel. In a further aspect of the present invention, the optical detection configuration may be scaled up and implemented in a multi-channel CE system that comprises multiple capillary separation channels.

30 Claims, 16 Drawing Sheets

U.S. PATENT DOCUMENTS

| | | | |
|---|---|---|---|
| 5,324,401 A | | 6/1994 | Yeung et al. |
| 5,338,427 A | | 8/1994 | Shartle et al. |
| 5,366,608 A | | 11/1994 | Kambara |
| 5,413,686 A | | 5/1995 | Klein et al. |
| 5,416,879 A | * | 5/1995 | Liu ............................ 385/125 |
| 5,439,578 A | | 8/1995 | Dovichi et al. |
| 5,444,807 A | * | 8/1995 | Liu ............................ 385/125 |
| 5,498,324 A | | 3/1996 | Yeung et al. |
| 5,529,679 A | | 6/1996 | Takahashi et al. |
| 5,543,018 A | | 8/1996 | Stevens et al. |
| 5,545,901 A | | 8/1996 | Pentoney, Jr. et al. |
| 5,560,811 A | | 10/1996 | Briggs et al. |
| 5,584,982 A | | 12/1996 | Dovichi et al. |
| 5,625,403 A | * | 4/1997 | Hazman et al. ............. 347/243 |
| 5,650,846 A | | 7/1997 | Yin et al. |
| 5,675,155 A | * | 10/1997 | Pentoney, Jr. et al. ... 250/458.1 |
| 5,741,411 A | | 4/1998 | Yeung et al. |
| 5,741,412 A | | 4/1998 | Dovichi et al. |
| 5,763,277 A | | 6/1998 | Zhu et al. |
| 5,790,727 A | | 8/1998 | Dhadwal et al. |
| 5,846,727 A | | 12/1998 | Soper et al. |
| 5,968,331 A | | 10/1999 | Kambara et al. |
| 6,001,230 A | | 12/1999 | Burolla |
| 6,008,055 A | * | 12/1999 | Zhu et al. ................... 436/172 |
| 6,027,627 A | | 2/2000 | Li et al. |
| 6,043,880 A | | 3/2000 | Andrews et al. |
| 6,054,032 A | | 4/2000 | Haddad et al. |
| 6,063,251 A | | 5/2000 | Kane et al. |
| 6,084,667 A | | 7/2000 | Melman et al. |
| 6,104,485 A | | 8/2000 | Wang et al. |
| 6,132,578 A | | 10/2000 | Kambara et al. |
| 6,153,437 A | | 11/2000 | Horn |
| 6,184,990 B1 | | 2/2001 | Amirkhanian et al. |
| 6,326,213 B1 | * | 12/2001 | Letcher et al. .............. 436/518 |

OTHER PUBLICATIONS

A Capillary Array Gel Electrophoresis System Using Multiple Laser Focusing for DNA Sequencing.

Researchers Design DNA Lab on a Chip.

Laser–Induced Fluorescence Detection of a Single Molecule in a Capillary.

Up to Speed on PCR.

Low–Cost, High–Sensitivity Laser–Induced Fluorescence Detection for DNA Sequencing by Capillary Gel Electrophoresis.

Electrophoresis, 1996, 17, 1845–1851.

"Demonstration of an Integrated Capillary Electrophoresis–Laser–Induced Fluorescence Fiber–Optic Sensor", by Sepaniak, et al., Talanta 43 (1996), pp. 1889–1901.

International Search Report of Counterpart PCT Application No. PCT/US02/20116.

* cited by examiner

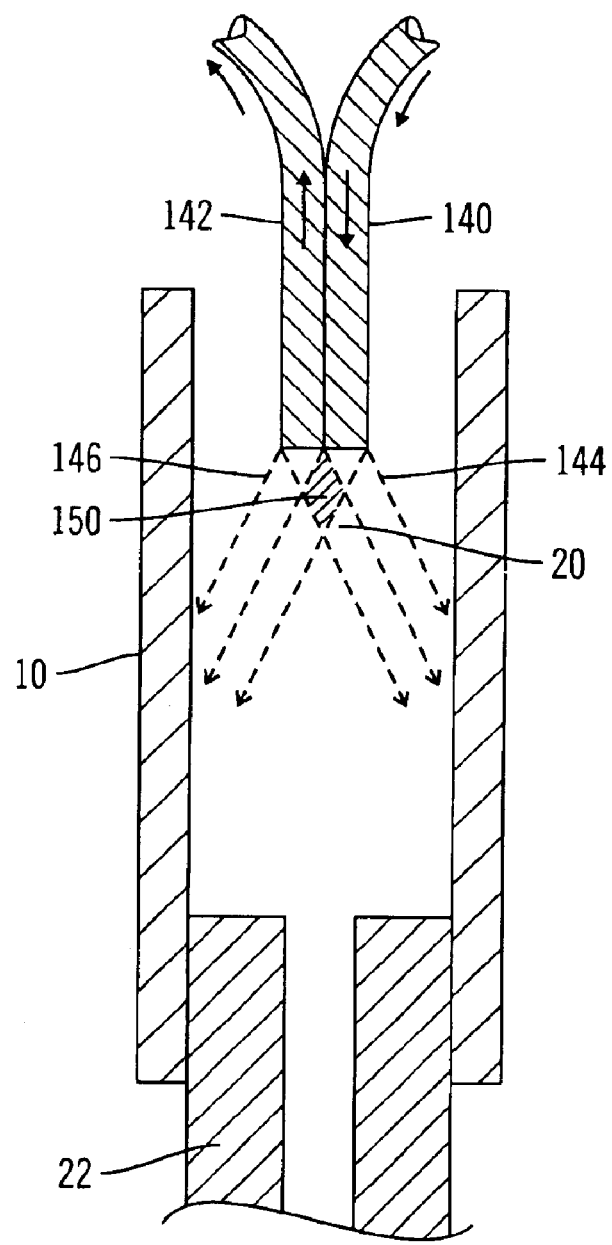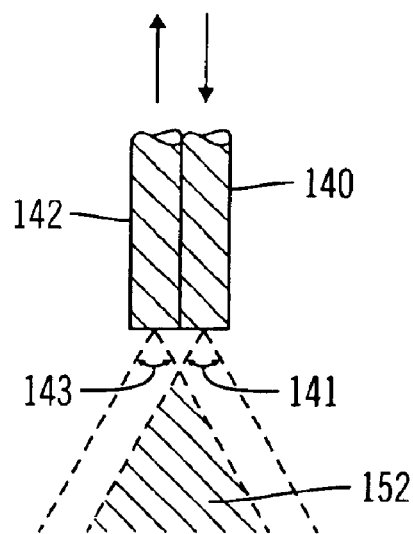
FIG. 10B
FIG. 10C

OPTICAL DETECTION IN BIO-SEPARATION DEVICE USING AXIAL RADIATION INPUT

BACKGROUND OF THE INVENTION

1. Cross-Reference

U.S. patent application Ser. No. 09/887,953 entitled Optical Detection in Bio-Separation Device Using Axial Radiation Output, concurrently filed on Jun. 22, 2001, and U.S. patent application Ser. No.09/887,872 entitled Optical Detection in Bio-Separation Device Using a Widened Detection Zone, concurrently filed on Jun. 22, 2001, which are commonly assigned to BioCal Technology, Inc., the assignee of the present invention, and which are fully incorporated by reference herein.

2. Field of the Invention

The present invention relates to detection techniques in bio-analysis, particularly optical detection in bio-separation through a separation column, and more particularly detection of emissions from radiation excitations in capillary electrophoresis.

3. Description of Related Art

Bioanalysis, such as DNA analysis, is rapidly making the transition from a purely scientific quest for accuracy to a routine procedure with increased, proven dependability. Medical researchers, pharmacologists, and forensic investigators all use DNA analysis in the pursuit of their tasks. Yet due to the complexity of the equipment that detects and measures DNA samples and the difficulty in preparing the samples, the existing DNA analysis procedures are often time-consuming and expensive. It is therefore desirable to reduce the size, number of parts, and cost of equipment, to make easy sample handling during the process, and in general, to have a simplified, low cost, high sensitivity detector.

One type of DNA analysis instruments separates DNA molecules by relying on electrophoresis. Electrophoresis techniques could be used to separate fragments of DNA for genotyping applications, including human identity testing, expression analysis, pathogen detection, mutation detection, and pharmacogenetics studies. The term electrophoresis refers to the movement of a charged molecule under the influence of an electric field. Electrophoresis can be used to separate molecules that have equivalent charge-to-mass ratios but different masses. DNA fragments are one example of such molecules.

There are a variety of commercially available instruments applying electrophoresis to analyze DNA samples. One such type is a multi-lane slab gel electrophoresis instrument, which as the name suggests, uses a slab of gel on which DNA samples are placed. Electric charges are applied across the gel slab, which cause the DNA sample to be separated into DNA fragments of different masses.

Another type of electrophoresis instruments is the capillary electrophoresis (CE) instrument. By applying electrophoresis in a fused silica capillary column carrying a buffer solution, the sample size requirement is significantly smaller and the speed of separation and resolution can be increased multiple times compared to the slab gel-electrophoresis method. These DNA fragments in CE are often detected by directing light through the capillary wall, at the components separating from the sample that has been tagged with a fluorescence material, and detecting the fluorescence emissions induced by the incident light. The intensities of the emission are representative of the concentration, amount and/or size of the components of the sample. In the past, Laser-induced fluorescence (LIF) detection methods had been developed for CE instruments. Fluorescence detection are often the detection method of choice in the fields of genomics and proteomics because of its outstanding sensitivity compared to other detection methods.

Some of the challenges in designing CE-based instruments and CE analysis protocols relates to sample detection techniques. In the case of fluorescence detection, considerable design considerations had been given to, for example, radiation source, optical detection, sensitivity and reliability of the detection, cost and reliability of the structure of the detection optics. In the past, relatively high power light source is required, such as Laser systems. When light is directed through the capillary wall at the separated sample components in the capillary bore, light scatters at the outside capillary walvair interface and the inside capillary wall/buffer interface (Raman scattering), which obscures or corrupts the fluorescence emission intensity. Similarly, fluorescence emissions scatter at the wall interfaces. In the past, various techniques were developed for more completely collecting the fluorescence emissions to improve signal intensity and hence detection sensitivity. These techniques involve additional moving and non-moving components that add to the relative complexity and cost of the detection setup.

The design limitations of prior art electrophoresis instruments are exacerbated in the development of multi-capillary CE-based instruments. For example, confocal scanning laser induced fluorescence (LIF) detection has been adopted in multi-capillary electrophoresis systems. The scanning confocal detection relies on a scanning optical system. The use of moving parts is not ideal when taking simplicity, robustness, and lower cost of the instrument into consideration. Also, the shallow focal depth of the microscope objective for the confocal detector puts severe demands on the mechanical and optical component tolerances. Further, the optical scanning method generally involves a longer duty cycle per capillary. Thus, should the instrument be scaled up in order to generate higher throughput, the sensitivity of the system may be impaired.

SUMMARY OF THE INVENTION

The present invention provides a simplified, low cost, efficient, highly sensitive, non-moving and stable micro-optical detection configuration for bio-separation (e.g., capillary electrophoresis) through a separation channel (e.g., defined by a column) filled with a separation support medium (e.g., a liquid or sieving gel including a running buffer). More particularly, the present invention is directed to an improved detection configuration for the detection of radiation emitted by sample analytes (e.g., fluorescence emission), in contrast to radiation absorbance detection techniques.

In one aspect of the present invention, incident radiation (e.g., from a laser or LED source) for the detection is directed at the detection zone axially (i.e., in the direction of the axis, but does not necessarily have to be along the axis) along the separation medium, instead of through the boundary walls of the detection zone or the separation column. In one embodiment, incident radiation is directed via an optic fiber (hereinafter referred to as an excitation fiber) that extends axially along the separation medium to the proximity of the detection zone. Emitted or output radiation from the detection zone passes through the boundary walls about the detection zone for detection (i.e., off-column detection).

According to one embodiment of off-column detection, a curved reflective collector is used to better capture and collect the emitted radiation, for example by using a parabolic, ellipsoidal, toroidal, or spherical reflector as a light collector. According to another embodiment of off-column detection, high collection angle micro-lenses are used to facilitate in capturing the maximum amount of emitted radiation.

According to another embodiment of the present invention, at least two excitation fibers direct incident radiation to provide incident radiation at different wavelengths.

According to a further embodiment of the present invention, at least two radiation sources direct radiation at different wavelengths to the detection zone via a single excitation fiber (e.g., by means of a dichroic beam combiner).

According to another embodiment of the present invention, at least two lasers and a beam combiner are combined with an excitation fiber, which is incorporated inside a micro-channel.

In another aspect of the present invention, emitted radiation signals representative of the sample components are collected from the detection zone axially along the separation medium (hereinafter referred as on-column detection), instead of through the boundary walls of the detection zone or the separation column (which is off-column detection). In one embodiment, emitted signals are collected via an optic fiber (hereinafter referred to as the emission fiber) that extends from the proximity of the detection zone along the separation medium.

According to another embodiment of the present invention, two fibers (an excitation fiber and an emission fiber) are incorporated into detection collar, one for excitation radiation and the other for emitted radiation detection.

According to a further embodiment of the present invention, confocal radiation detection optics is configured to make use of a single dual-purpose (excitation and emission) fiber to direct incident radiation at the detection zone and emitted radiation from the detection zone to a detector. An optical element (e.g., a beam splitter such as a dichroic beam combiner) is employed to direct incident radiation from a source at the detection zone through the single dual-purpose fiber, and to separate the emitted radiation from the detection zone arriving through with the same dual-purpose fiber.

Various combinations of the foregoing embodiments of detection configurations may be implemented without departing from the scope and spirit of the present invention. For example, using a combination of dual-purpose fiber, excitation fiber and/or emission fiber, a combination of on-column and off-column detection at different wavelengths of incident radiations may be configured.

In another aspect of the present invention, the zone for optical detection of sample components is located at a widened zone along the separation channel. In one embodiment of the present invention, the widened detection zone is a micro-bore collar having a micro-channel that coaxially surrounds the exit of a capillary column that defines a capillary channel. A separation support medium (e.g., a liquid or sieving gel) including a running buffer fills the capillary column and the collar.

According to yet another embodiment of the present invention, excitation radiation is directed at the detection zone from outside the walls of the widened detection zone, with on-column or off-column optical detection.

In a further aspect of the present invention, the optical detection of the present invention may be scaled up and implemented in a multi-channel CE system that comprises multiple capillary separation channels, using similar axial incident radiation and/or emitted radiation detection configurations set forth above.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

FIG. 10B is an axial sectional view taken along line 10B—10B in FIG. 10A.

FIG. 10C is an alternate sectional view of the excitation and collection fibers as in FIG. 10B.

DETAILED DESCRIPTION OF THE PREFERRED EMBODIMENTS

Figure 1:
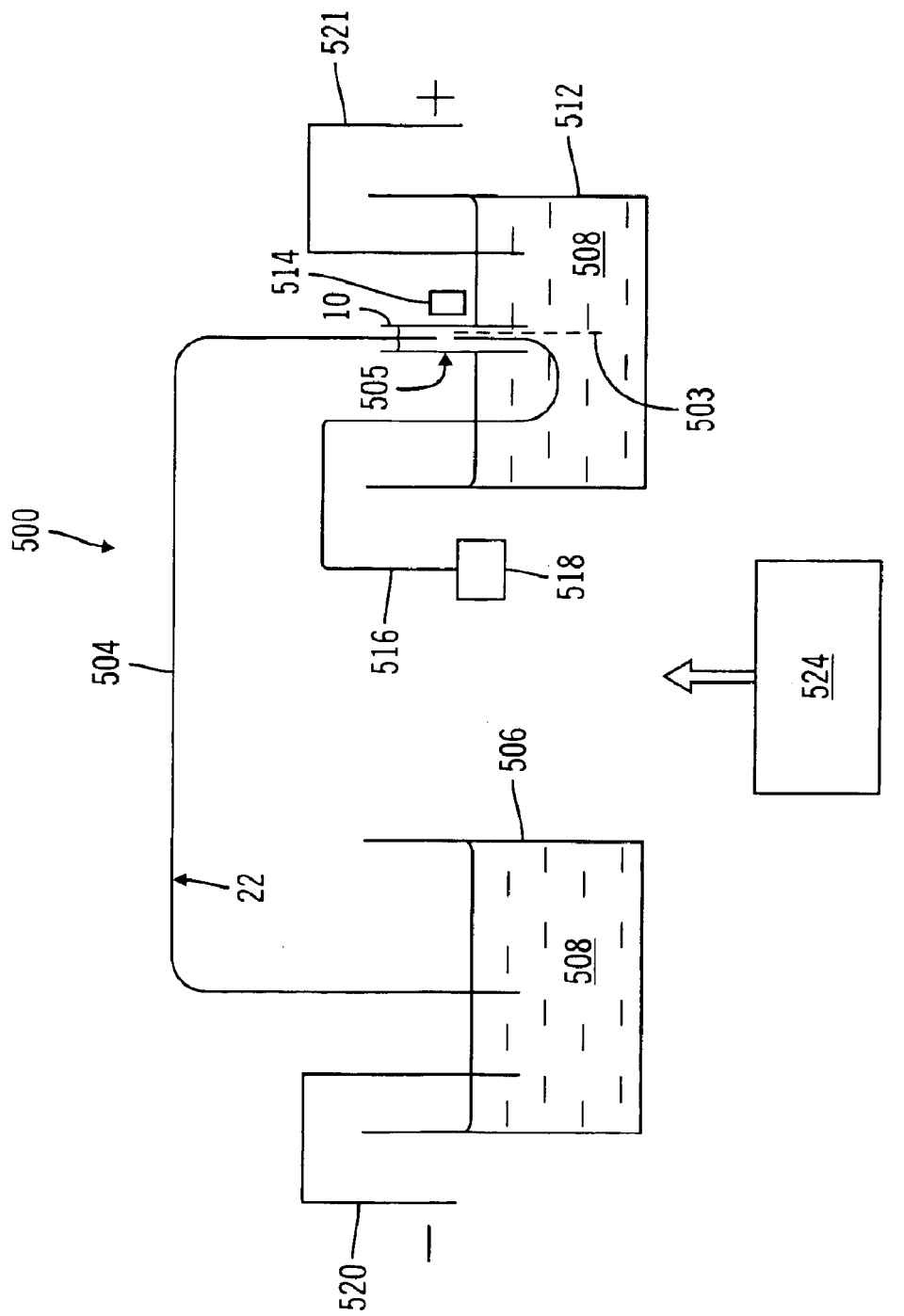
FIG. 1 is a schematic view of a capillary electrophoresis system that incorporates the optical detection concept of the present invention.

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention is directed to a novel detection configuration in which incident radiation (e.g., from a laser or LED source) for detection of separated analytes is directed at the detection zone axially along the separation medium (i.e., in the direction of the axis of the separation channel, but does not necessarily have to be along the axis), instead of through the boundary walls of the detection zone or the separation column. For purpose of illustrating the principles of the present invention and not limitation, the present invention is described by reference to embodiments directed to capillary electrophoresis, radiation induced fluorescence, and a separation channel having a widened detection zone.

Detection at Widened Separation Channel Section

Radiation emission detection, on which the present invention is based, can be contrasted with radiation absorbance detection. Radiation absorbance detection techniques are well known in the art. They involve directing an incident radiation at analytes in the detection zone, and measuring the amount or intensity of radiation that passes through the analytes, or the equivalent decrease in intensity or the amount of radiation that is absorbed by the analytes (i.e., the attenuation of the incident radiation). For emissive radiation detection as in the present invention, the detection is based on a different phenomenon. The amount or intensity of radiation that is emitted from the analytes (radiated by a radiation source) is being detected (not the attenuation of the incident radiation), representative of the characteristic of the analytes and the interaction with the particular radiation source in emitting radiation. Radiation emission may result from dissipation of radiant energy as a result of a change of energy states of the target material in the presence of the incident radiation. Radiation emission may also result from other types of interaction of the target material in response to incident radiation.

The present invention will be described, without limitation, in connection with radiation induced fluorescence detection. Fluorescence is a spectrophotometric method of analysis where the molecules of the analytes are excited by irradiation at a certain wavelength and emit radiation at a different wavelength. The emission spectrum provides information for both qualitative and quantitative analysis. Generally, the advantage of fluorescence detection over absorbance detection is the superior detectability (detection sensitivity). For efficient fluorophores, single molecule detection in small volumes has been demonstrated. This is in part because fluorescence signal is measured against a relatively dark background, as a result of the emitted radiation being detected at a wavelength that is different from the wavelength of the incident radiation (e.g., the wavelength of the emitted fluorescence is at longer wavelengths than the excitation radiation). This is in contrast to absorbance detection, in which attenuation is measured at the same wavelength as the incident radiation, and where a small decrease of the total light intensity is measured (i.e., comparing two relatively large signals, thus giving rise to a limiting noise that is the shot noise of the total light intensity). The sensitivity of fluorescence techniques can be as much as 1000 times more sensitive than absorption spectroscopy. It is understood that the scope of the present invention is not limited to detection of fluorescence type of emission, but is also applicable to detection of other types of emissive radiation as compared to radiation absorption, such as phosphorescence, luminescence and chemiluminescence.

Referring to FIG. 1, a capillary electrophoresis system 500 that incorporates the present invention is schematically illustrated. The CE system 500 generally comprises a capillary separation column 22 (e.g., 200–500 μm O.D.), which defines a separation channel 504 (e.g., 25–150 μm I.D.). The capillary column 22 may be made of fused silica, glass, polyimide, or other ceramic/glassy materials. The inside walls of the separation column 22 (i.e., the walls of the separation channel 504) may be coated with a material that can build up an electrostatic charge to facilitate electrophoresis and/or electrokinetic migration of the sample components. The separation channel 504 is filled with a separation support medium, which may be simply a running buffer, or a sieving gel matrix known in the art.

Figure 12:
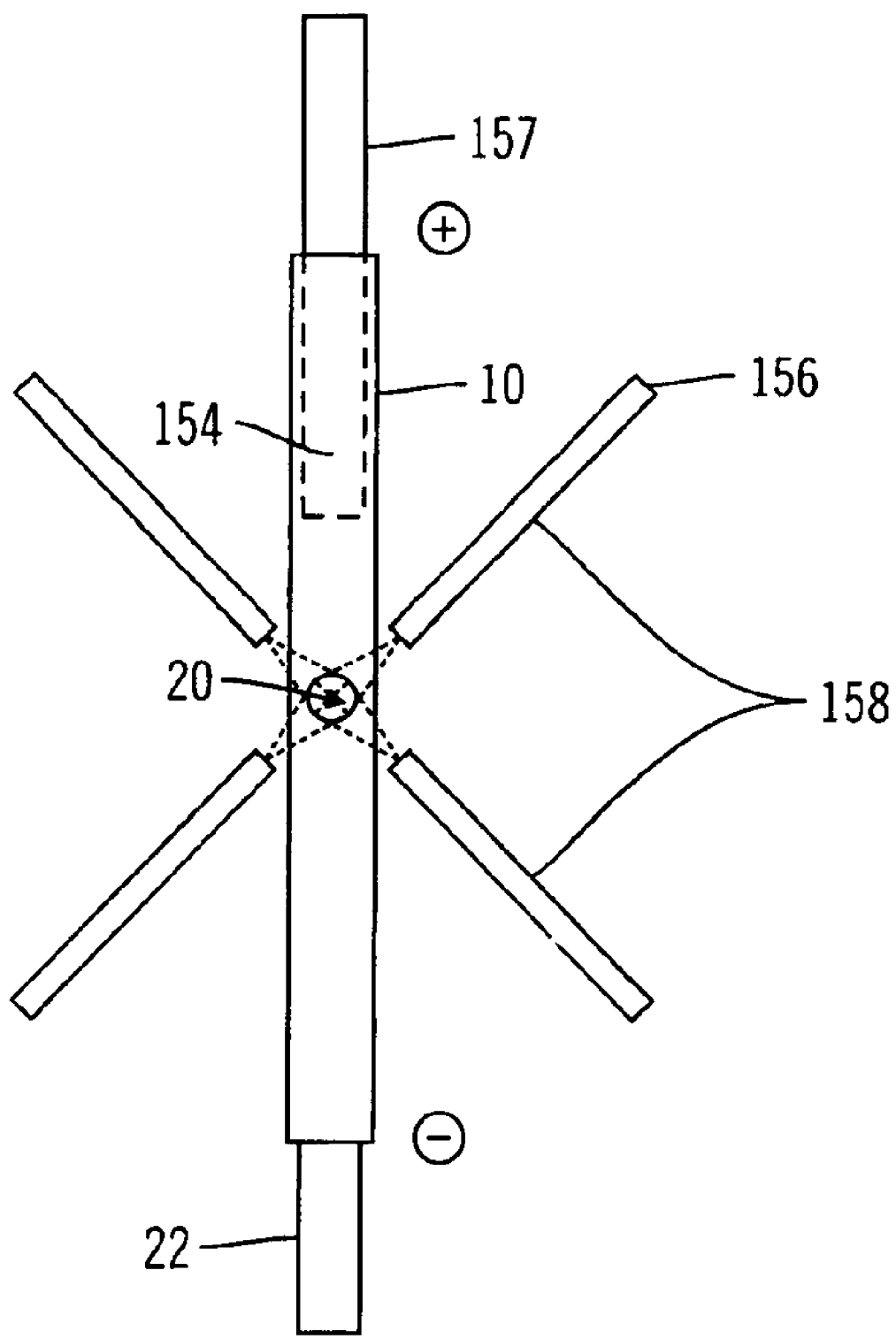
FIG. 12 is a perspective view of an axial detection configuration using multiple excitation in accordance with another embodiment of the present invention.
Figure 13:
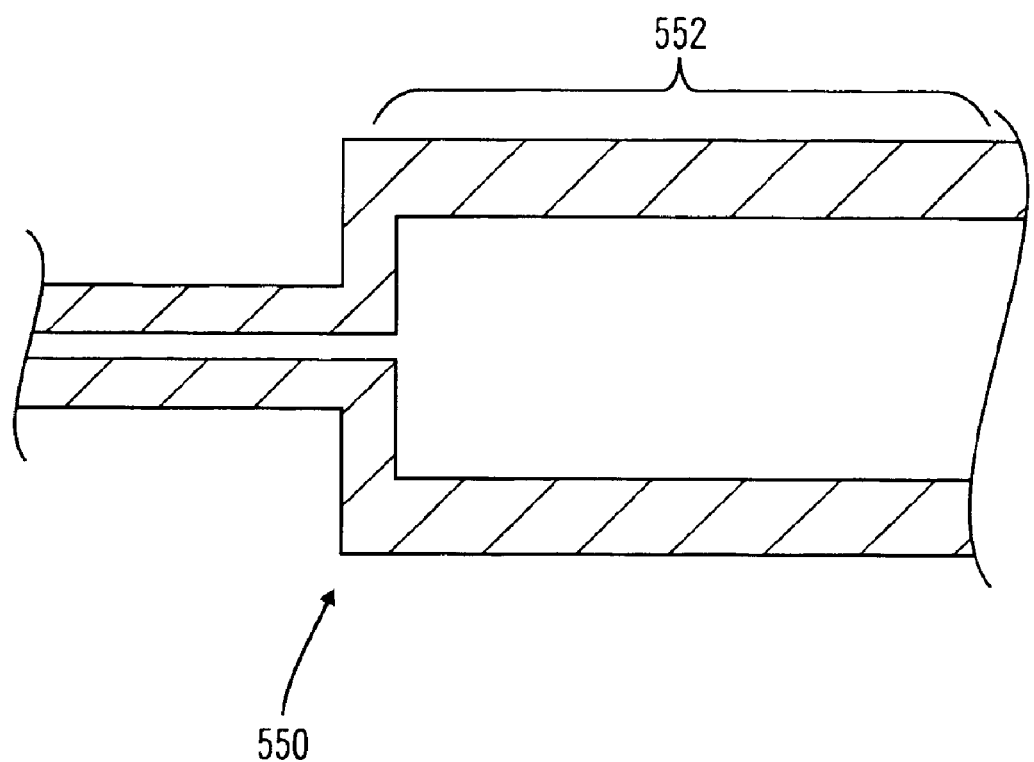
FIG. 13 is axial section view of a capillary separation column having an unitary enlarged detection section.

One end of the capillary column 22 is submerged in a reservoir 506 of running buffer 508. The other end of the capillary column 22 is coupled to a widened section 505 that defines a detection zone in accordance with the present invention. (U.S. patent application Ser. No. 09/887,872, entitled Optical Detection in Bio-Separation Device Using a Widened Detection Zone, concurrently filed on Jun. 22, 2001, which is commonly assigned to BioCal Technology, Inc., the assignee of the present invention, and which has been fully incorporated by reference herein, is more specifically directed to the widened detection zone concept.) In the particular illustrated embodiment in FIG. 1, the detection configuration corresponds to the embodiment illustrated in FIG. 2. It is understood that the detection configurations shown in the other embodiments can be equally implemented in a system similar to the CE system 500. The widened section 505 is schematically shown to be a separate collar 10 in FIG. 1. In one embodiment of the present invention, the widened detection zone is a micro-bore collar having a micro-channel that coaxially surrounds the exit of a capillary column 22. (It is within the scope of the present invention to use a unitary capillary column 550 having a widened section 552, as illustrated in FIG. 13, or other configurations to define a widened detection region without departing from the scope and spirit of the present invention.) The end of the collar 10 that is not coupled to the capillary column 22 is submerged into a buffer reservoir 512. A radiation detector 514 is positioned outside a transparent section of the walls of the collar 10 (i.e., in an off-column detection configuration). (In an on-column detection configuration in the embodiments explained later, the collar may have opaque walls to prevent loss of emitted radiation from the detection zone.) An excitation fiber 516 extends from a radiation source (e.g., LED or laser) into the collar 10, to direct radiation at the detection zone. Depending on the collimation optics, the end of the excitation fiber 516 may be positioned at or proximate to the detection zone. (Alternatively, as illustrated in FIG. 12, the excitation radiation may be directed at the detection zone using excitation fibers outside of the walls of the detection zone.) Electrodes 520 and 521 are coupled to the buffer reservoirs.

The mechanism of electrophoresis and radiation induced fluorescence when considered alone are outside the scope of the present invention. For the sake of completeness, it is sufficient to briefly mention the operation of the CE system 500. In operation, a prepared biological sample (e.g., a DNA sample), tagged with a known fluorophore, is introduced into the far end of the capillary column away from the detection zone, by any of a number of ways that is not part of the present invention (e.g., electrokinetic injection from a sample reservoir or physical pressure injection using a syringe pump). When a DC potential (e.g., 1–30 KV) is applied between electrodes 520 and 521, the sample migrates under the applied electric potential along the separation channel 504 (e.g. DNA that is negatively charged travels toward a positive electrode as shown in FIG. 1) and separates into bands of sample components. The extent of separation and distance moved along the separation channel 504 depends on a number of factors, such as migration mobility of the sample components, the mass and size or length of the sample components, and the separation support medium. The driving forces in the separation channel 504 for the separation of samples could be electrophoretic, pressure, or electro-osmotic flow (EOF) means.

When the sample reaches the detection zone, excitation radiation is directed via the excitation fiber 516 at the detection zone. The sample components would fluoresce with intensities proportional to the concentrations of the respective sample components (proportional to the amount of fluorescent tag material). The detector 514 detects the intensities of the emitted fluorescence, at a wavelength different from that of the incident radiation. The detected emitted radiation may be analyzed by known methods. For an automated system, a controller 524 controls the operations of the CE system 500.

The widened detection section 505 provides a configuration for better interaction between excitation radiation and the analytes tagged with the fluorophores in the widened detection zone. This results in the emission of more fluorescence signals, thus improving signal-to-noise ratio and detection sensitivity. The widened detection zone also provides physical space to accommodate detection optics to more efficiently direct incident and/or emitted radiation to and from the detection zone (e.g., using optic fiber for incident and/or emitted radiation as discussed herein below).

Axial Excitation

Figure 2A:
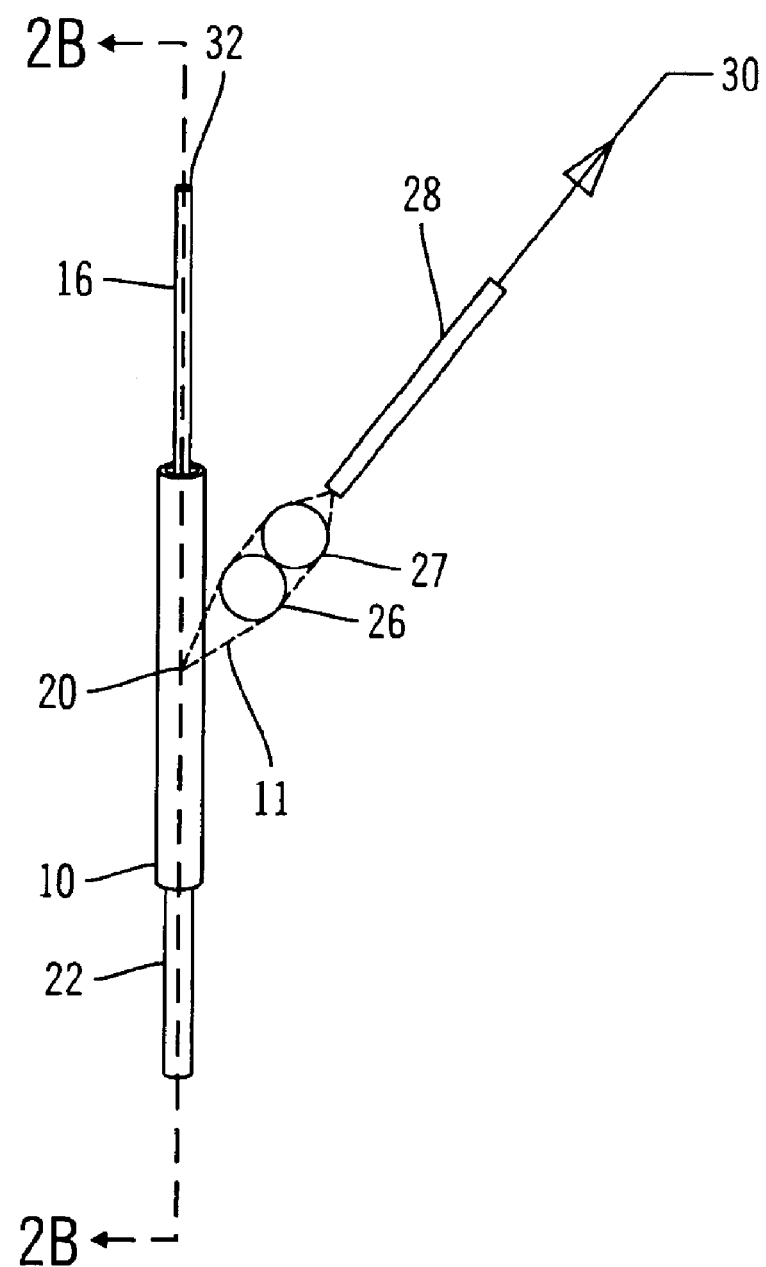
FIG. 2A is a perspective view of a detection configuration using axial excitation at the detection collar in accordance with one embodiment of the present invention.
Figure 2B:
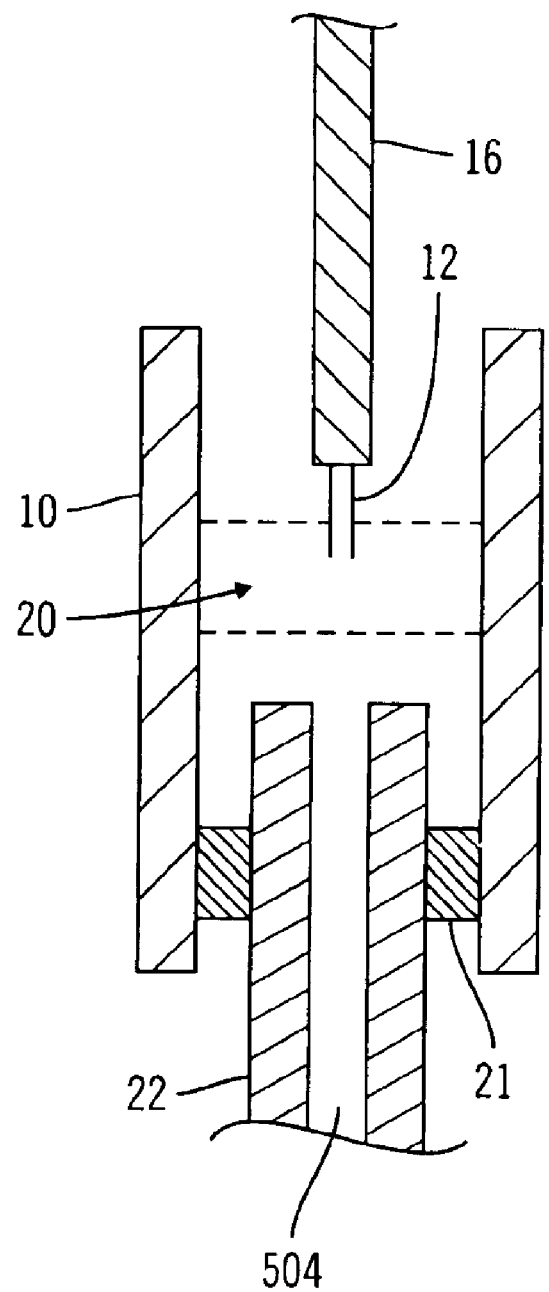
FIG. 2B is an axial sectional view taken along line 2A—2A in FIG. 2B.

FIG. 2A–2B show in greater detail the novel detection scheme in accordance with one inventive aspect of the present invention. (The figures show the detection end of the separation channel 504 of the capillary column 22, with the vertical orientation of the separation column 22 inverted compared to FIG. 1.) The collar 10 (e.g., 200 to 400 $\mu$m ID) is filled with a separation support medium, including a liquid buffer or a sieving gel. The capillary column 22 extends into one end of the collar 10. The coaxial structure of the capillary column 22 and the collar 10 may be configured in one of several ways. For example, the outside diameter of the capillary column 22 and the inside diameter of the collar 10 may be selected to provide a tolerance fit. Alternatively, annular seals 21 (e.g. UV epoxy or mechanical seal) may be provided to retain fluid in the collar, as shown in FIG. 2B. Depending on the vertical orientation of the capillary column 22 and the collar, similar seals may be provided at the excitation fiber end, in addition or in the alternate to seals at the capillary column end. It is noted that because of the capillary/micro-bore nature of the collar 10, the fluid in the collar 10 could be well retained by capillary and/or surface tension actions without requiring any seals (for example in the orientation shown in FIG. 1).

The excitation light 12 (e.g., 524 nm wavelength for a fluorphore of the type, Ethidium Bromide) from a light source 32 (not shown) is directed at the detection zone 20 defined by the collar 10, using the excitation fiber 16 (e.g., having 50 to 300 $\mu$m OD) at its focal point. No collimation optics for collimating the excitation beam is needed since the fiber 16 is inside the liquid or gel and the fiber's focal point is in close proximity to the detection zone 20. The fiber 16 could be mechanically centered inside the micro-bore channel (this is not crucial) or it could be placed to one side. The Numerical Aperture of the fiber determines the amount of power density launched inside the gel close to detection zone 20. The excitation light source 32 may be a LED, which is relatively inexpensive, or a laser (may be solid state laser, gas laser, dye laser or the like). The fluorescence emissions 11 from the separated components or analyte at the detection zone 20 is collected through micro-lenses 26 and 27 and directed through an emission collection fiber 28 to a detector 30 (not shown). The collar 10 may have transparent walls, or opaque walls provided with a transparent window to direct emissions to the micro-lens 26. The lens 26 is used for collecting emissions and preferably has a high collection angle property (e.g., a sapphire micro-lens with index of refraction of n=1.76 from Swiss Jewel Company Model # B2.00), that has a short focal distance with a high numerical aperture (N.A.)). The lens 27 is for coupling the collimated emission light produced by the sapphire lens to the emission fiber 28 (e.g., a BK-7 micro-lens, available from the Swiss Jewel Co.). The fluorescent light, which has a higher wavelength (e.g., 570 to 630 nm) than the excitation light, is then routed by a large core optical fiber (370 $\mu$m OD, 0.22 NA fibers, but could also be in ranges of: 100–1000 um OD, 0.12–0.5 NA) to a detector (e.g., R5984 Hamamatsu photomultiplier tube (PMT)) after going through color separation (e.g., using 570–610 nm) long pass emission filters. The collection of the fluorescence emissions may also be achieved from inside the collar (on-column detection, see for example FIG. 5) as an alternative to the off-column detection shown here.

It is noted that as the analytes flow from the separation channel 504 of capillary column 22 into the collar 10, the analytes remain subject to the applied potential. As a result, the analytes continue to maintain separation state (i.e., in the form of a series of separate analyte bands) as they migrate/flow past the detection zone 20. Some mixing or diffusion of the analytes may occur in the collar near the exit of the separation channel 504, but analytes "regroup" into separated state as they continue down along the collar 10 towards the detection zone 20. The detection zone 20 is preferably located at 100–500×ID of the collar 10, more like 225 times the ID, to provide sufficient distance for the analytes to regroup before detection at the detection zone 20. Because the diameter of the detection zone is larger than the diameter of the separation channel 504, the analyte bands are narrower in the axial direction. Thus the detection resolution may be improved as a result.

It is further noted that the detection zone is not necessarily a well-defined zone with well-defined boundaries, due to the nature of the substance, the incident radiation, and the fluorescence emissions. It is generally a zone in which light 12 from the excitation fiber 16 is directed to cause fluorescence emissions 11 and the detection optics is aimed to capture part of such fluorescence emissions 11. Light 12 from the excitation fiber 16 may cause fluorescence emissions outside the detection zone, and some of the emissions from within the zone may not be detected by the detection optics. The closer the excitation fiber is to the detection zone or the higher the power density of excitation light, the stronger the collected emission signals are. Also, since the excitation light is coaxial with the separation column and it is off-axis from the detection optics, then less background or excitation energy is coupled/leaked into the detector. And since the excitation fiber is inside the gel or buffer, it is more index-matched, and there is no air interface, then less light scattering (which means proportionally less background) leads to lower detection noise or better signal/noise or detection sensitivity.

Figure 3:
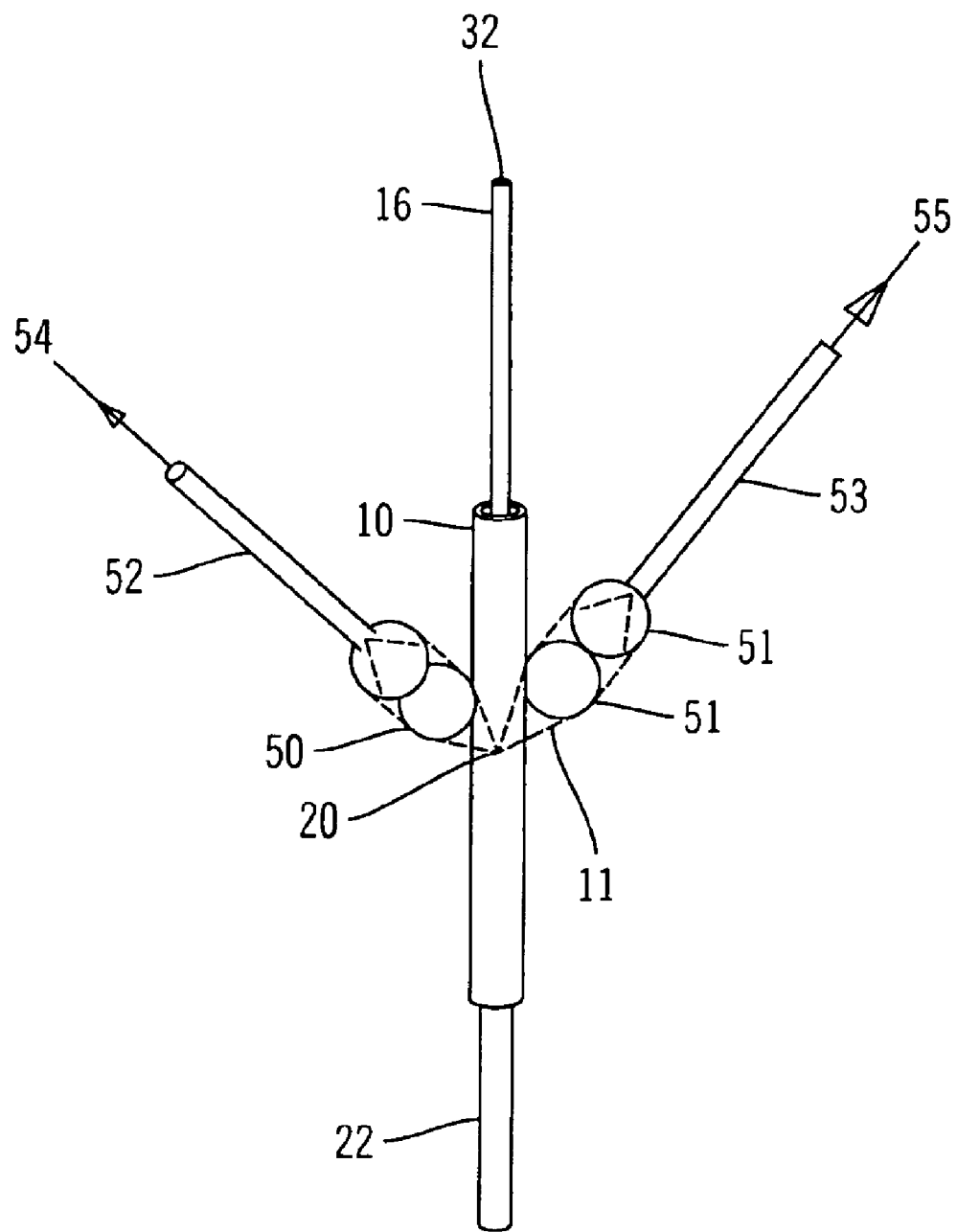
FIG. 3 is a perspective view of a detection configuration using multiple external collection fibers for multi-wavelength optical detection in accordance with one embodiment of the present invention.

According to another embodiment of the present invention, the detection configuration in FIG. 2A is modified to allow off-column fluorescence detection from two or more sides of the collar channel. In FIG. 3, micro-lenses 50 and 51 collect fluorescence emissions from the analytes as they pass through the detection zone 20, and direct the emissions to collection fibers 52 and 53 and to detectors 54 and 55, respectively. By using additional set(s) of collection optics, more of the emissions are collected to increase the sensitivity and resolution of the detected signals. By providing detectors that detect emissions having different wavelengths, a multi-wavelength detection scheme can be implemented for detecting different types of analytes that have been preferentially tagged with different materials that fluoresce at different emission wavelengths. If the analytes are being excited axially from inside the separation/microchannels a CCD camera could also be placed or used from outside of the capillaries to detect emission signals from multiple channels.

Figure 4:
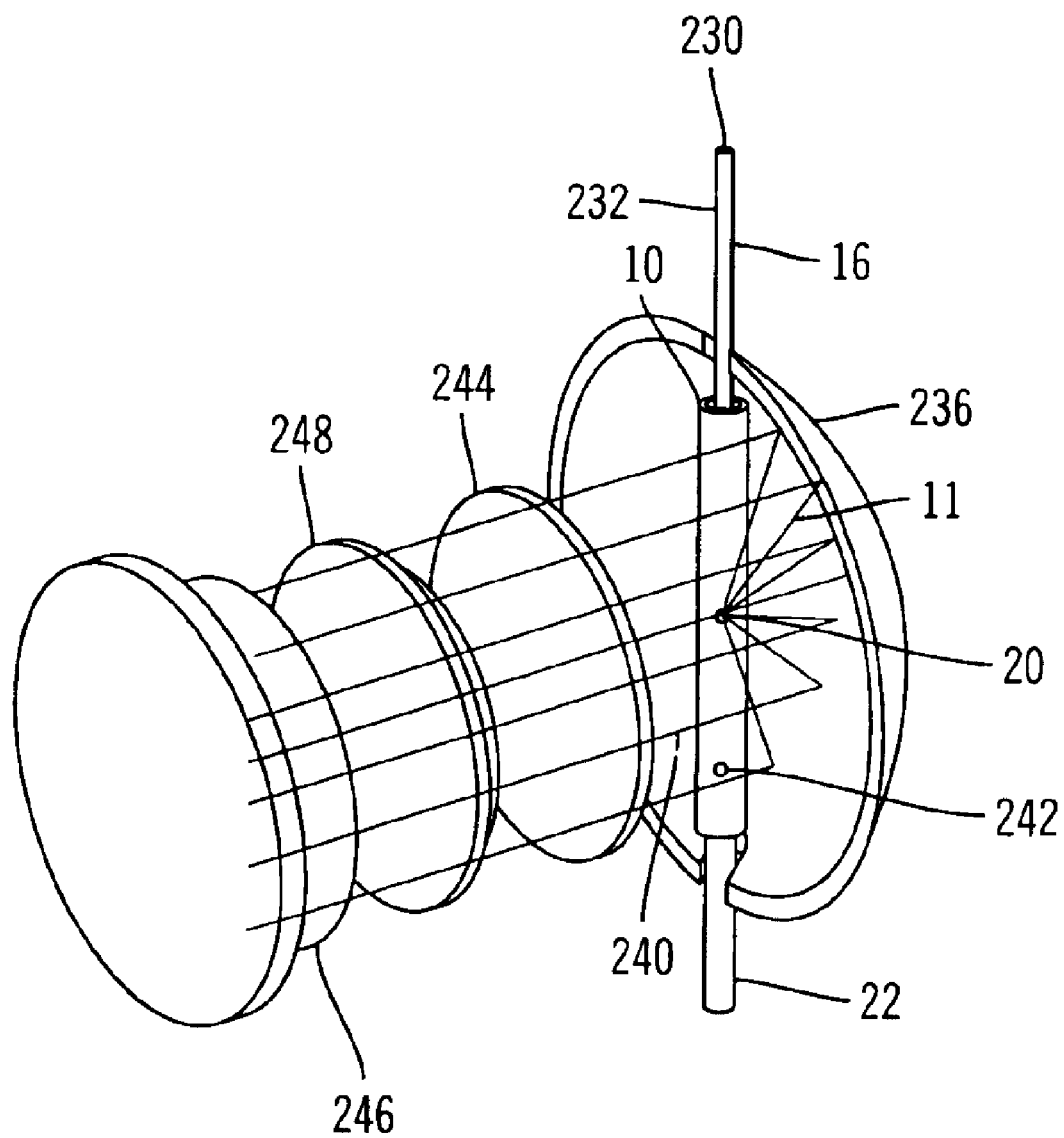
FIG. 4 is a perspective view of a detection configuration using a concave reflective emission collector in accordance with one embodiment of the present invention.

Another embodiment of off-column detection is illustrated in FIG. 4. In this embodiment, the detection optics in FIG. 2 is modified to include a concave reflective collector 236. Compared to a collector lens, the concave collector 236 spans over a relatively large area to better capture and collect the fluorescence emissions 11 from the detection zone 20. The concave collector 236 may be parabolic, ellipsoidal, toroidal, or spherical in shape, having a mirror or a polished concave surface. For a concave collector 236 that is parabolic, with the detection zone 20 at the focal point of the parabolic reflector, the emissions 11 are collimated. The collimated light beams 240 are passed through emission filter 244 and focusing lens 248, to a photodiode or PMT detector 246. Compound parabolic collectors and integrating sphere type collectors (not shown) could also be used in the alternative.

Figure 5:
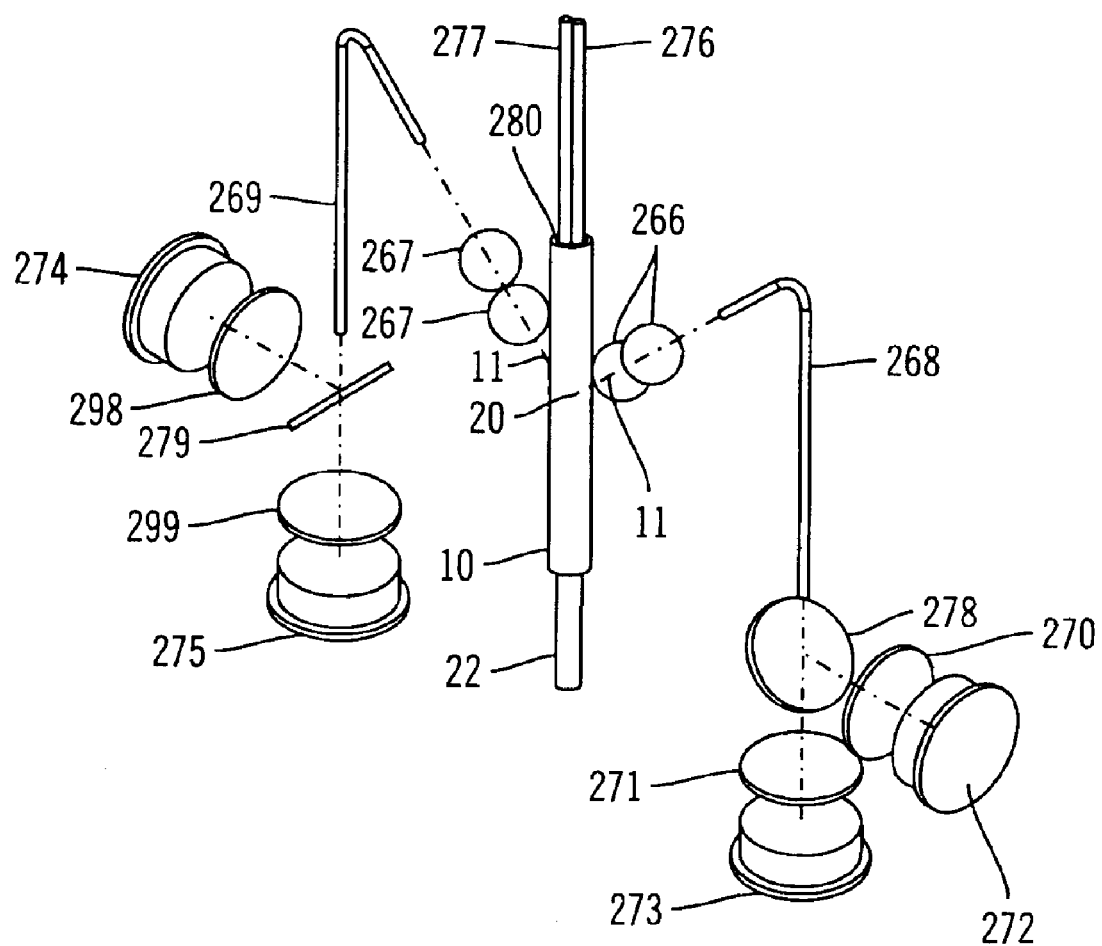
FIG. 5 is a perspective view of a detection collar having two axial excitation fibers for dual-wavelength excitation in accordance with one embodiment of the present invention.

According to another embodiment of the present invention, at least two excitation fibers direct incident radiation to provide incident radiation at different wavelengths. FIG. 5 shows the configuration of two excitation fibers 276 and 277 that direct excitation radiation axially to the collar 10. Emission collection may be accomplished from the outside of the detection zone 20 in a manner similar to that in FIG. 3, using two sets of micro-lenses 266 and 267 and emission fibers 268 and 269 to direct the emissions 11. Unlike FIG. 3, the emissions are directed from the emission fibers 268 and 269 to beam splitters 278 and 279. The light is then directed to emission filters 270, 271, 298 and 299 and to detectors 272, 273, 274, and 275, respectively. Each detector detects light having a different wavelength, $\lambda_1$, $\lambda_2$, $\lambda_3$, and $\lambda_4$, respectively. This embodiment can be used as a DNA sequencer to detect four DNA bases A, T, C, and G by appropriately tagging the sample with fluorophores that preferentially attach to the bases and fluoresce at the four different wavelengths in response to the incident radiation at two wavelengths.

Figure 6:
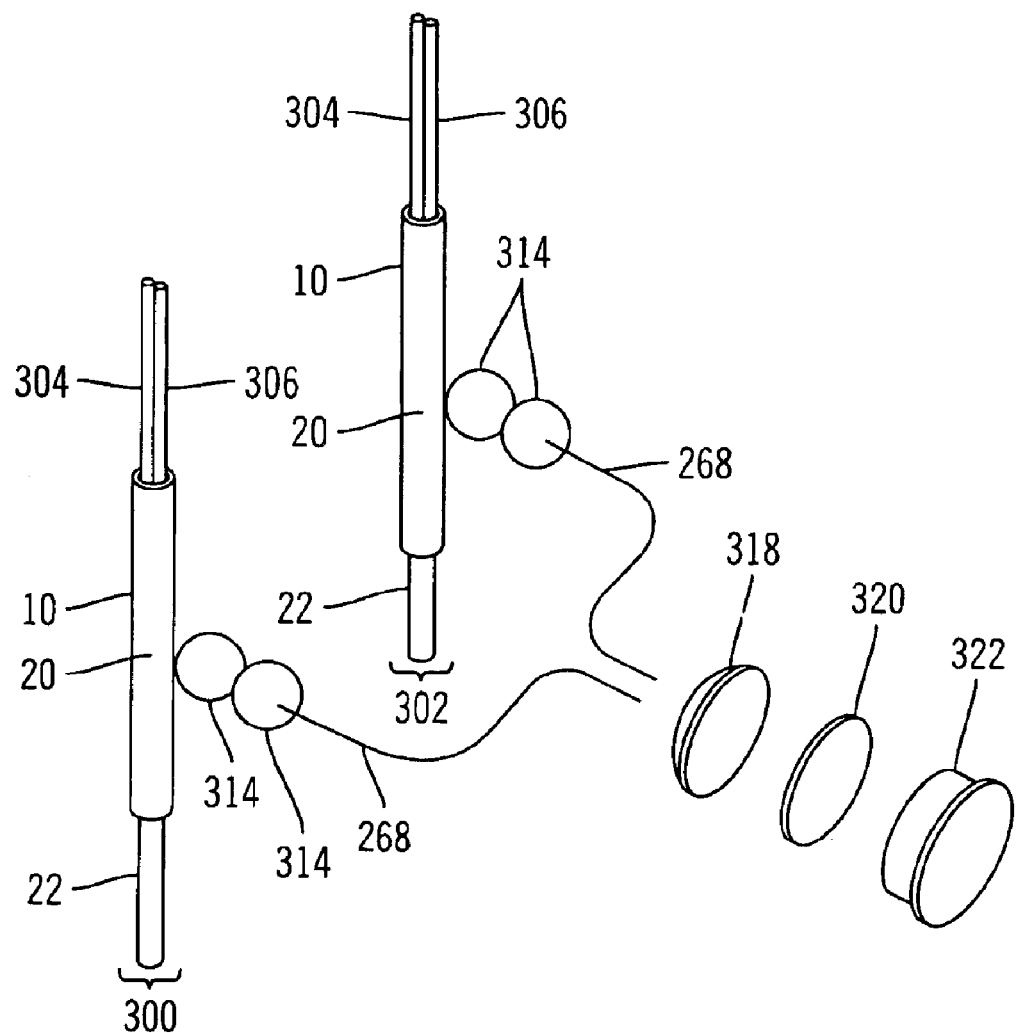
FIG. 6 is a perspective view of another embodiment of a multi-wavelength detection configuration.

The detection configuration in FIG. 5 may be extended to a system in which there are multiple separation channels and multiple wavelength excitation and detection. In FIG. 6, there are two parallel separation channels 300 and 302, each with an excitation fiber arrangement similar to FIG. 5. Each channel comprises a collar 10, two excitation fibers 304 and 306 directing light at different wavelengths $\lambda_1$, and $\lambda_2$, respectively, into the collar 10 to the detection zone 20. The excitation wavelengths of the excitation fibers may be different between channels in addition to being different within the same channel (i.e., at four excitation wavelengths overall). The fluorescence emissions from each channel are collected using optics 314 similar to FIG. 5, but a single detector 322 is used in combination with four emission filters 320 and a condensing lens 318 for multi-wavelength detection. With this system, it can detect four different types of fluorophores that are reactive to two or four wavelengths to fluoresce in four different wavelengths.

Figure 7:
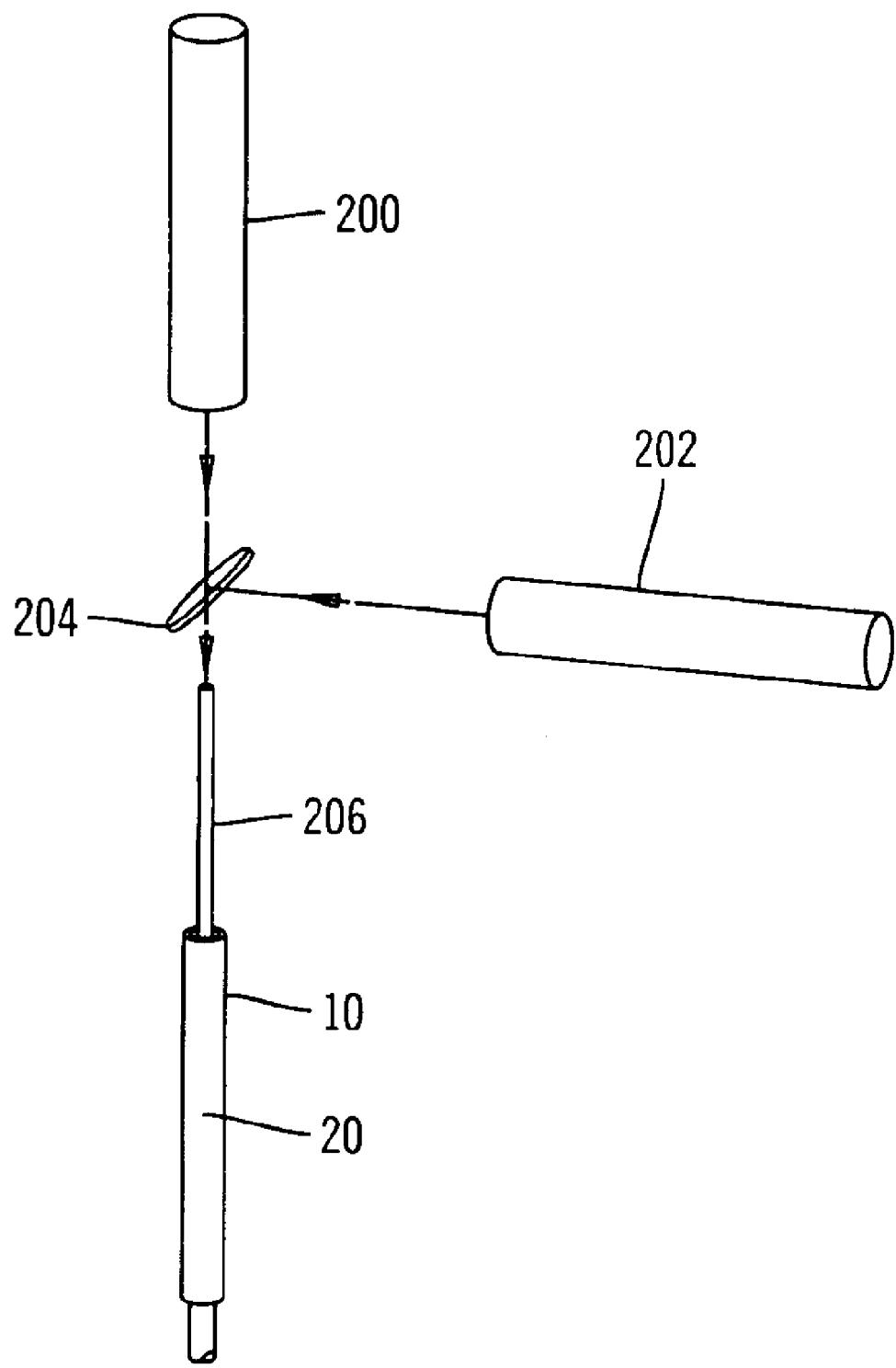
FIG. 7 is a perspective view of a detection system in which light from multiple excitation source are combined into one excitation fiber in accordance with one embodiment of the present invention.

Referring to FIG. 7, according to a further embodiment of the present invention, at least two radiation sources direct radiation at different wavelengths to the detection zone via a single excitation fiber. Lasers 200 and 202 with wavelengths $\lambda_1$ and $\lambda_2$, respectively, are used in this embodiment. A beam splitter/combiner 204, such as dichroic beam combiner (or a fiber optic coupler/combiner not shown in the sketch), optically combines the collimated beams from the lasers and directs it through a single excitation fiber 206 to the detection zone (excitation area) 20. The detection optics (omitted in FIG. 7) may be any one of those off-column detection configurations described in the foregoing embodiments, or the on-column detection configurations described below.

Figure 8:
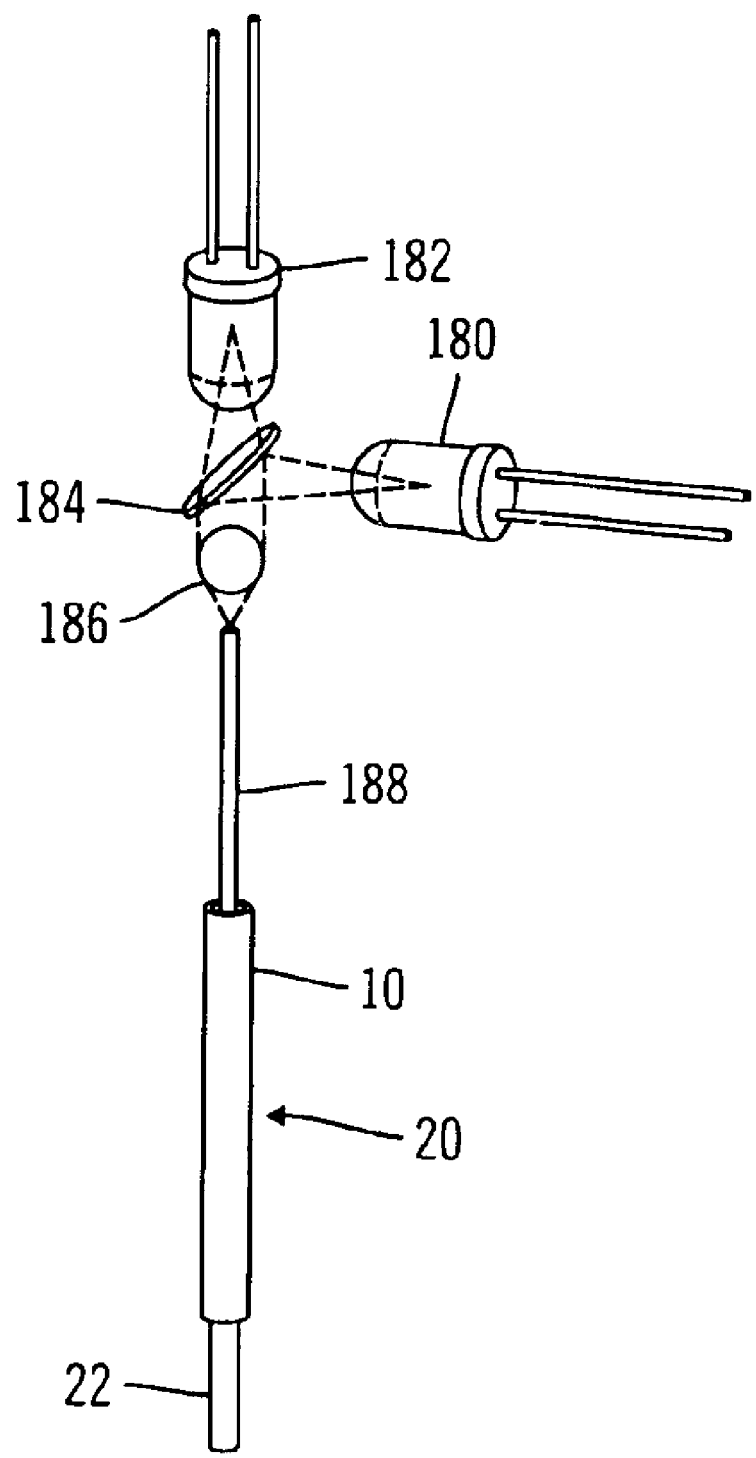
FIG. 8 is a perspective view of another embodiment of a multi-wavelength single excitation fiber detection configuration.

FIG. 8 shows another embodiment of a multi-wavelength excitation configuration. At least two LEDs 180 and 182 and a beam splitter (dichroic beam combiner or fiber coupler) 184 are combined with an excitation fiber 188. The LEDs 180 and 182 produce light at wavelengths $\lambda_1$ and $\lambda_2$, respectively, which are optically combined by a focusing micro-ball lens 186 and directed at the collar 10 via a single excitation fiber 188. The detection optics (omitted in FIG. 8) may be any one of those off-column detection configurations described in the foregoing embodiments, or the on-column detection configurations described below.

Figure 9A:
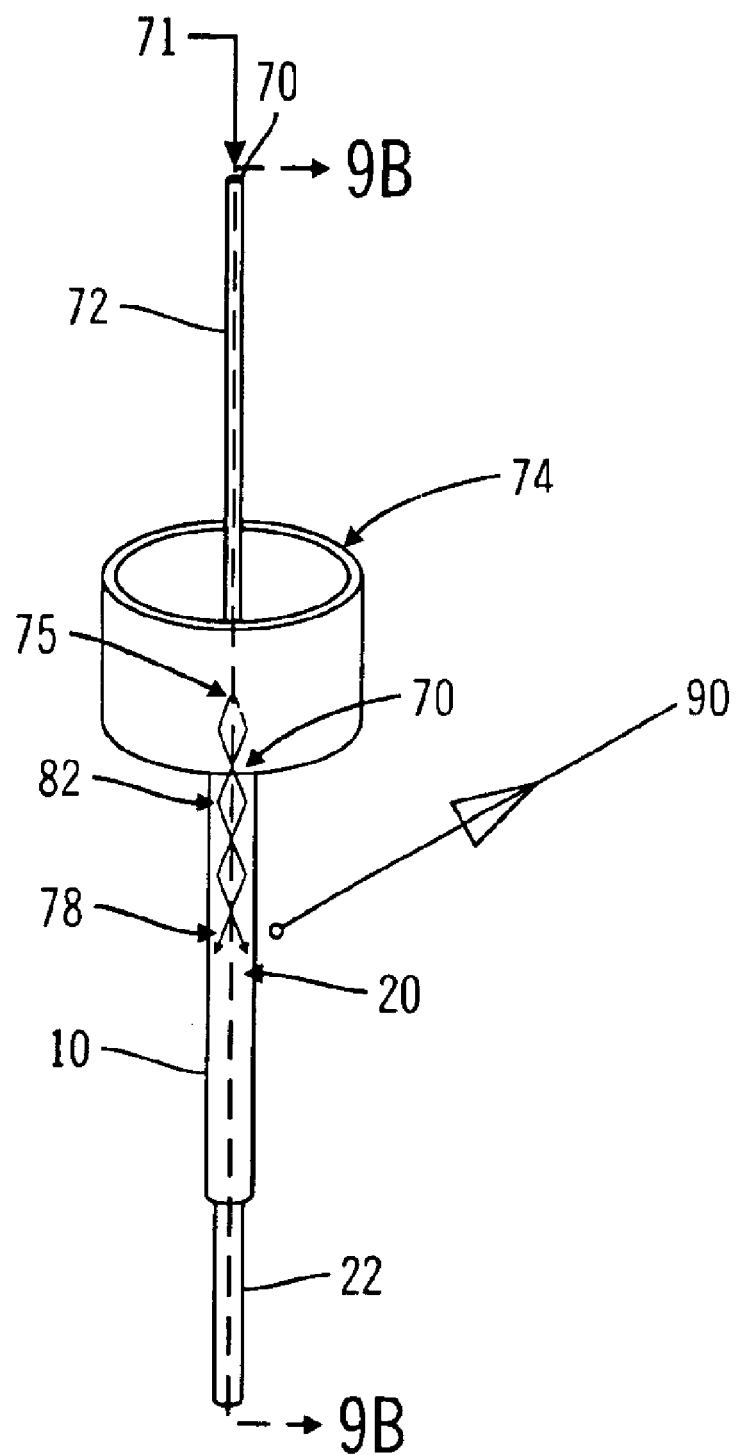
FIG. 9A is a perspective view of a detection configuration having an insert in the detection collar in accordance with one embodiment of the present invention.
Figure 9B:
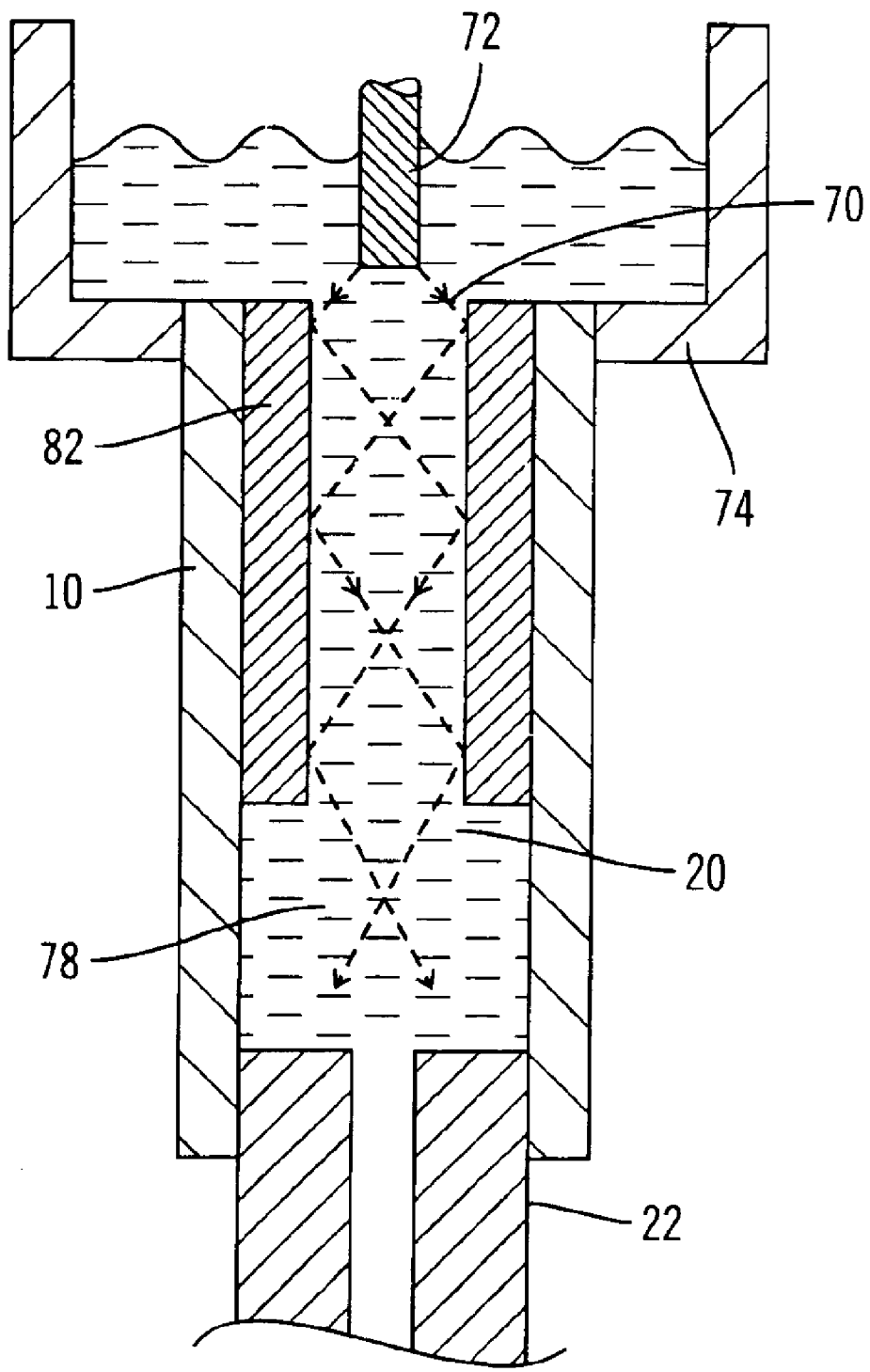
FIG. 9B is an axial sectional view taken along line 9B—9B in FIG. 9A.

According to another embodiment of the present invention as shown in FIG. 9A, a light source 71 provides an excitation beam 70 that is wave-guided to the detection zone 20 using an insert in the collar 10 and relying on the total internal reflection (TIR) phenomenon. TIR is implemented by inserting a Teflon (polytetrafluorethylene) fluoropolymer hollow tubing 82 inside the collar 10. The hollow tubing 82 acts like a cladding in a liquid waveguide and has a lower index of refraction than the core (the liquid gel or buffer). The tubing 82 creates the TIR effect inside the liquid waveguide, which very efficiently directs the excitation light to the detection zone. The excitation fiber 72 has its end submerged in a reservoir 74 or gel 78. The gel 78 has a refractive index of about 1.35, which is lower than the refractive index of the optical fiber, which is about 1.46. However, the refractive index of fluoropolymer (n=1.29) is lower than the refractive index of gel (n=1.35) and lower than that of water (n=1.33), which is also used as a liquid waveguide, with water as its core material for illumination purposes/applications. Therefore, light directed throughout the gel would not totally reflect (TIR) from at the inner wall of the collar 10, but when light is directed through the fluoropolymer tube, it would totally reflect at the Teflon/gel boundary. The excitation light 70 refracts at an angle a before entering the tubing 82. Through TIR within the Teflon tube 82, the excitation light 70 is brought from the top of the collar 10 to the detection zone 20. Another advantage of this embodiment is that by placing the end of the excitation fiber inside the sieving gel 78, there is lower excitation light scattering at the end of the Teflon tube from which light enters due to index matching of the excitation fiber 72 with the gel 78.

In an air interface, the index of refraction is 1, which can create high refractions going from a high index to a low index material. In a "liquid" interface, with a gel index of 1.35, the glass fiber with a core index of 1.46 is closer, resulting in less refraction, less scattering, better waveguiding, and better beam direction. Since the excitation is not done from the outside of the collar there is no lens/glass-to-air boundary, which means less scattering and more efficient coupling of excitation light to the detection zone; thus, there is less background and better detection sensitivity.

Various combinations of the foregoing embodiments of off-column detection configurations may be implemented without departing from the scope and spirit of the present invention. For example, using a combination of dual-purpose fiber, excitation fiber and/or emission fiber, a combination of off-column detection at different wavelengths of incident radiations may be configured.

Axial incident excitation in accordance with the present invention results in emission signals that are higher intensities and better resolution, because the incident excitation is directed at the detection more directly compared to the prior art methods in which light is directed through the walls of the separation column with more scattering and higher detected background. In other CE-based system in which the excitation fiber is brought into close proximity of the glass capillary at the detection region, due to the refractive index and geometry of the glass capillary, light scattering takes place that could obscure or contaminate the emissions from the detection zone. This scattering directly translates to higher background noise detected by the detector and affects the overall detection sensitivity.

On-Column Detection

Figure 10A:
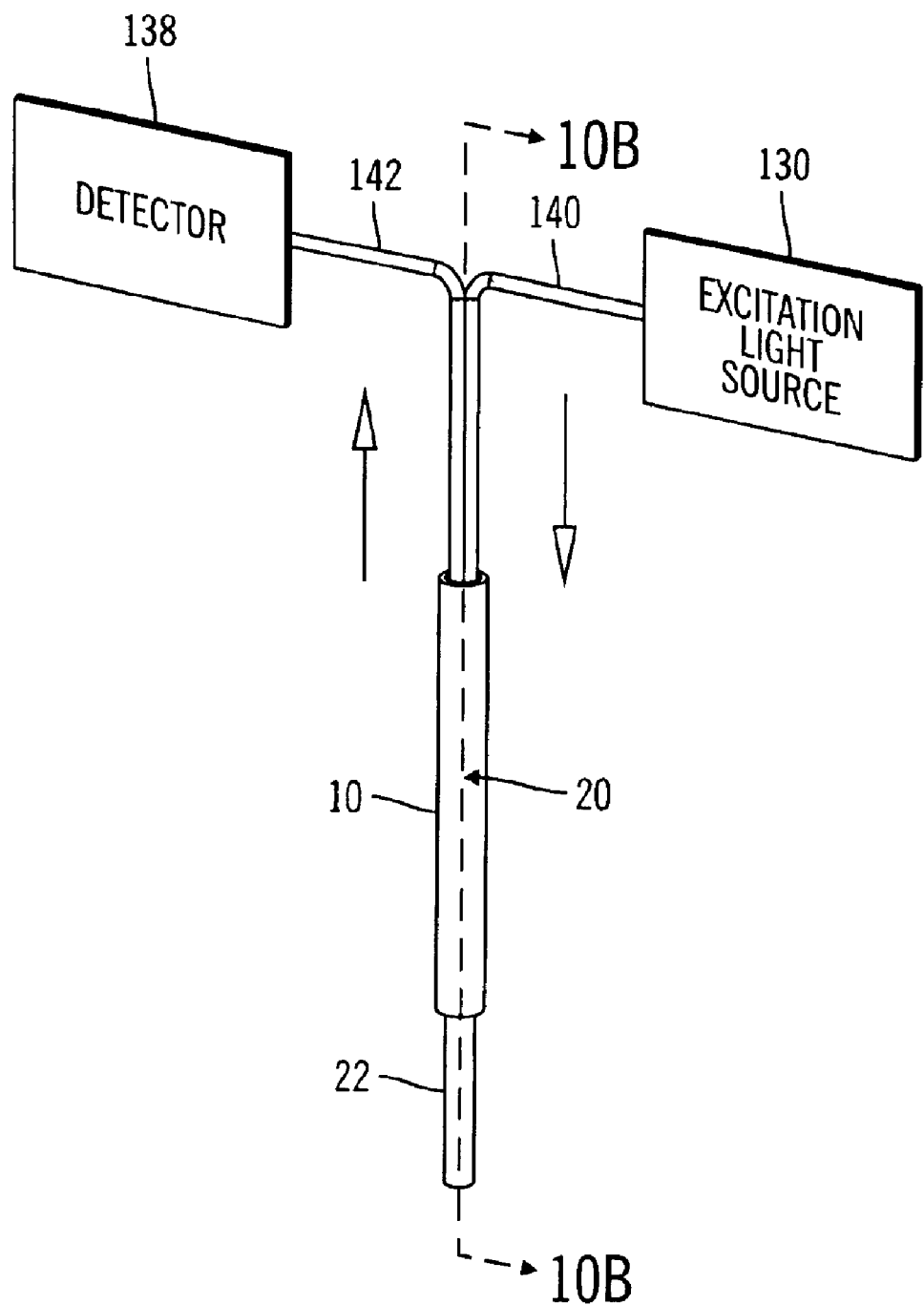
FIG. 10A is a perspective view of a detection configuration using axial excitation and detection in accordance with one embodiment of the present invention.

In another aspect of the present invention, emitted radiation signals representative of the sample components are collected from the detection zone axially along the separation medium (i.e., on-column detection), for example along dotted line 503 schematically shown in FIG. 1, instead of through the boundary walls of the detection zone or the capillary channel (which is off-column detection). In one embodiment illustrated in FIGS. 10A and 10B, two fibers (an excitation fiber and an emission fiber) are incorporated into detection collar, one for excitation radiation and the other for emitted radiation detection. The two fibers 140 and 142 are inserted inside the detection collar 10 and proximate to the detection zone 20. One fiber 140 is the excitation fiber that delivers excitation light 144 from the excitation light source 130 to the detection zone 20. The other fiber 142 is an emission fiber that collects emissions 146 from sample analytes in the detection zone 20 and directed at the detector 138.

The two fibers of excitation and emission collection are in close proximity to each other (closely packed together) so that a portion of the NA of the excitation fiber (0.22 NA or 24 degrees) is within the viewing angle (NA) of the collection fiber (0.22 NA or larger). As the separated fragments of DNA get close to the NA overlap region of the two fibers at the detection zone the detection/collection fiber picks up the maximum emission signal. Another approach would be to have the NA 143 or size of collection fiber 142 to be larger than the NA 141 of the excitation fiber 140 to increase emission collection capability, as shown in FIG. 10C with overlap region 152. This kind of fiber sensing is commonly done in fiber optic based sensing instruments for applications of color detection, temperature, pressure or strain sensing, working under the concept of intensity modulated fiber based sensors.

The light source 130 and detector 138 may be any suitable radiation detector, including additional complementary optical elements. By collecting emissions within the separation medium instead of through the walls of the collar, detection noise arising from scattering at the wall/medium and/or wall/air interfaces can be avoided. As long as the two fibers are closely packed they always go together, which means no optical alignment is necessary. This allows simpler detection, ease of manufacturing, and lower cost. Other arrangements of fibers for increasing signal collection can also be used (i.e. fiber bundles, different fiber geometries, or different fiber positioning arrangements).

Figure 11:
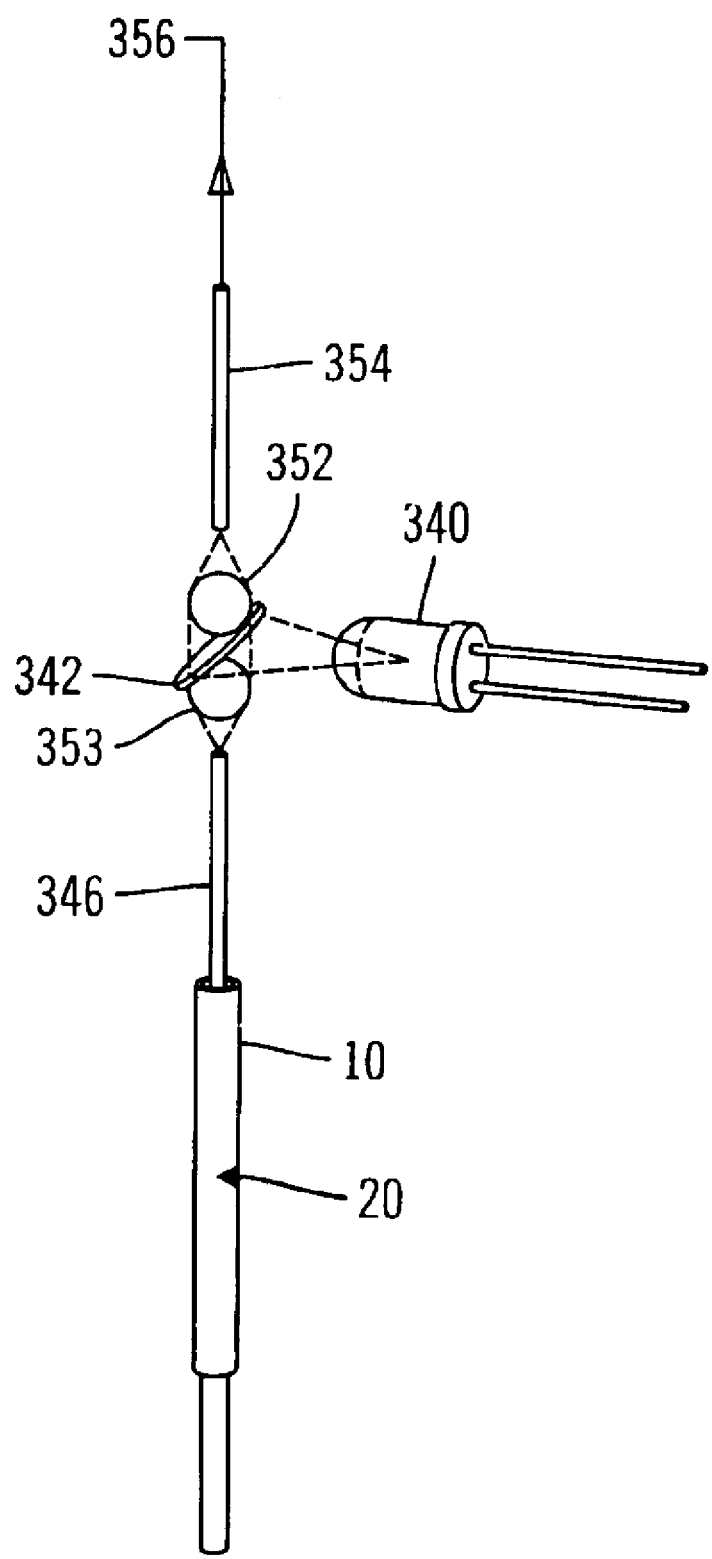
FIG. 11 is a perspective view of a confocal axial detection configuration in accordance with one embodiment of the present invention.

According to a further embodiment of the present invention, confocal radiation detection optics is configured to make use of a single dual-purpose (excitation and emission) fiber to direct incident radiation at the detection zone and emitted radiation from the detection zone to a detector. An optical element is employed to direct incident radiation from a source at the detection zone through the single dual-purpose fiber, and to separate the emitted radiation from the detection zone arriving through the same dual-purpose fiber. FIG. 11 shows a confocal configuration in which a dual-purpose (excitation and emission collection) fiber 346 is inserted into the detection collar 10. The excitation light from a light source 340 (e.g., LED or laser) directs the light to a beam splitter (dichroic beam combiner) 342 and to a focusing lens 353, which directs the light through the dual-purpose fiber 346 to the detection zone 20 inside collar 10. Emissions from the detection zone 20 is collected by the fiber 346 (now serving as an emission collection fiber), through the beam splitter 342, a focusing lens 352, and an emission collection fiber 354 to a detector 356. It is noted that this system is confocal in the sense that the incident radiation and the radiation emission shares the same focal point with respect to the micro-ball lens 353 and the fiber 346.

While the figures show axially directed excitation radiation using an excitation fiber 140 inside the collar 10, it is contemplated that the axial detection concept of the present invention may be applied to systems in which excitation radiation is directed through the walls of the detection zone 20. According to yet another embodiment of the present invention, excitation radiation is directed at the detection zone from outside the walls of the widened detection zone, with on-column or off-column optical detection. In FIG. 12, light from four LEDs or lasers 156 is directed through the sides of the collar 10. Detection is via an axial emission fiber 157 directed at the detection zone 20 as in the earlier embodiments. This arrangement of excitation fibers 158 increases the delivered excitation energy, thus increasing detection sensitivity.

U.S. patent application Ser. No. 09/877,953 (entitled Optical Detection in Bio-Separation Device Using Axial Radiation Output, concurrently filed on Jun. 22, 2001, which is commonly assigned to BioCal Technology, Inc., the assignee of the present invention, and which has been filly incorporated by reference herein) is more specifically directed to the novel on-column axial detection concept.

The present invention provides a simplified, low cost, efficient, highly sensitive, non-moving and stable micro-optical detection configuration to be used in a CE-based instrument. The detection configuration could also be used in instruments based on other types of separation techniques such as High Pressure Liquid Chromatography applications. The present invention utilizes low cost and miniature LEDs as excitation sources. Other non-coherent, broadband light sources could be used (i.e., xenon lamps, D2 lamps, mercury lamps, arc lamps). The emissions from the detection zone are collected by micro-optical lenses with fiber delivery systems either from outside or inside the detection collar. While the embodiments are described with reference to a separate detection collar 10, it is understood that the widened section of the detection zone may be defined by an unitary capillary column construction as the example shown in FIG. 13 without departing from the scope and spirit of the present invention.

Multi-Channel System

In a further aspect of the present invention, the optical detection of the present invention may be scaled up and implemented in a multi-channel CE system that comprises multiple capillary separation channels, using similar axial incident radiation and/or emitted radiation detection configurations set forth above. By simplifying the optical detection system design and the multi-channel cartridge approach, the cost, reliability, and ease of use of the instrument is improved. References are made to U.S. Provisional Application Nos. 60/264,553 and 60/264,605 both filed on Jan. 26, 2001; which disclosed a multi-channel, single detector, multiplexed detection system and a multi-channel cartridge. That system and cartridge may be modified to implement the detection scheme disclosed in the present application, and are fully incorporated by reference as if fully set forth herein.

While the invention has been particularly shown and described with reference to the preferred embodiments, it will be understood by those skilled in the art that various changes in form and detail may be made without departing from the spirit, scope, and teaching of the invention. For example, the excitation radiation source could be, for example, LEDs, Laser Diodes (semiconductor solid-state lasers), pulsed lasers (e.g., solid state lasers, gas lasers, dye lasers, fiber lasers), or other sources of radiation. LEDs (e.g., Green, 524 nm) are associated with low cost, super brightness, and small package. Alternate relative inexpensive light source for the present invention could be laser diodes in the visible, UV and/or infared range. For example, laser diodes in the range of 400–900 nm, and more specifically in the range of 400–600 nm may be used, for example.

A person skilled in the art will recognize that the instrument incorporating the essence of this invention can also be used for biomoleculer analysis other than DNA analysis. For example, by altering the separation gel or buffer, the system can also be modified to analyze biomolecules like proteins, carbohydrates, and lipids.

By way of example and not limitation, the detection scheme of the present invention is described in connection with capillary electrophoresis and radiation induced fluorescence detection. Further, as illustrative embodiments, the detection zone is defined in a widened section of the separation channel. It is understood that the present invention is also applicable to detection of analytes separated based on bio-separation phenomenon other than electrophoresis, and detection of radiation emissions other than fluorescence emissions. The detection zone may be uniform with the separation channel and still allow for axially directing incident excitation radiation and/or axially detecting radiation emissions.

Furthermore, while the separation channels in the described embodiments are defined by cylindrical columns or tubes, it is understood that the concepts of the present invention is equally applicable to separation channels defined by open channels, for example micro-channels defined by etching in a substrate.

Accordingly, the disclosed invention is to be considered merely as illustrative and limited in scope only as specified in the appended claims.

I claim:

1. A detection system for a bio-separation device, comprising:

a separation channel having an exit and a first width;

a detection section having a second width larger than the first width of the separation channel, wherein flow from the separation channel exits from the exit of the separation channel into the detection section, and wherein mixing or diffusion of analytes occurs near the exit of the separation channel;

an excitation system introducing excitation radiation axially at a location along the detection section defining a detection zone as analytes pass the detection zone, said location being defined at a distance of 100 to 500 times the second width of the detection section from the exit of the separation channel, thereby allowing analytes sufficient distance to regroup from the mixing or diffusion near the exit of the separation channel, said excitation system including an optic fiber having an end in close proximity to the detection zone; and a detector system detecting radiation emission from the detection zone.

2. The detection system as in claim 1, wherein the excitation system comprises a fiber that is directed into an end of the detection section in proximity to the detection zone.

3. The detection section as in claim 2, wherein the excitation radiation is provided at one wavelength.

4. The detection system as in claim 2, further comprising a light transmitting material disposed between the fiber and the detection zone to guide excitation radiation to the detection zone.

5. The detection system as in claim 4, wherein the excitation system further comprises a boundary material that surrounds the light transmitting material and guides the excitation radiation from the fiber to the detection zone.

6. The detection system as in claim 5, wherein the light transmitting material has a refractive index greater than the refractive index of the boundary material to guide the excitation radiation from the fiber to the detection zone by internal reflection.

7. The detection system as in claim 6, wherein the boundary material is embodied in a tube.

8. The detection system as in claim 7, wherein the tube is made of polytetraflurothylene and the light transmitting material comprises a gel.

9. The detection system as in claim 1, wherein the excitation radiation is provided at at least two wavelengths.

10. The detection system as in claim 9, wherein the excitation system comprises at least two radiation sources providing radiation at different wavelengths.

11. The detection system as in claim 10, wherein the excitation system comprises an optical element that channels the radiation from the two radiation sources into a single fiber directed at the detection zone.

12. The detection system as in claim 11, wherein the optical element comprises a beam splitter.

13. The detection system as in claim 11, wherein the radiation sources comprise Light Emitting Diodes.

14. The detection system as in claim 11, wherein the radiation sources comprise lasers.

15. The detection system as in claim 10, wherein the excitation system comprises two fibers directed at the detection zone, wherein each fiber is coupled to a different one of the at least two radiation sources.

16. The detection system as in claim 1, wherein the detector system comprises a radiation transmitting structure directing radiation emission axially from the detection zone.

17. The detection system as in claim 16, wherein the radiation transmitting structure comprises a fiber that is directed into an end of the detection section in proximity to the detection zone.

18. The detection system as in claim 17, wherein the detector system shares the same single fiber as the excitation system to transmit excitation radiation and radiation emission.

19. The detection system as in claim 18, further comprising a confocal optical element that transmits excitation radiation and radiation emission.

20. The detection system as in claim 19, wherein the confocal optical element comprises micro-lenses.

21. The detection system as in claim 19, wherein the confocal optical element comprises a beam combiner.

22. The detection system as in claim 1, wherein the detector system comprises a set of micro-lenses.

23. The detection system as in claim 1, wherein the detector system comprises a curved reflective collector.

24. The detection system as in claim 23, wherein the curved reflective collector comprises one of a parabolic, ellipsoidal, toroidal, or spherical reflector.

25. The detection system as in claim 1 wherein the excitation system comprises a radiation source and a light transmitting material disposed between the radiation source and the detection zone to guide excitation radiation to the detection zone.

26. The detection system as in claim 25 wherein the excitation system further comprises a boundary material that surrounds the light transmitting material and guides the excitation radiation to the detection zone.

27. The detection system as in claim 1 wherein the analytes comprise a material that fluoresces in the presence of the excitation radiation, and the detector system comprises a detector detecting fluorescence emission of the material.

28. The detection system as in claim 1 wherein the radiation emission is at least one of:

fluorescence;

chemiluminescence; or phosphorescence.

29. A bio-separation instrument, comprising:

a separation channel having a first width and an exit;

a separation system separating a sample in the separation channel into analytes; and a detection system, comprising:

(a) a detection section having a second width larger than the first width of the separation channel wherein flow from the separation channel exits from the exit of the separation channel into the detection section, and wherein mixing or diffusion of analytes occurs near the exit of the separation channel;

(b) a radiation system introducing excitation radiation axially at a location along the detection section defining a detection zone as analytes pass the detection zone, said location being defined at a distance of 100 to 500 times the second width of the detection section from the exit of the separation channel, thereby allowing analytes sufficient distance to regroup from the mixing or diffusion near the exit of the separation channel, said radiation system including an optic fiber having an end in close proximity to the detection zone; and (c) a detector system detecting radiation emission from the detection zone.

30. A bio-separation instrument as in claim 29, wherein the separation channel is defined by a capillary column, and the separation system is configured to effect separation of the sample by electrophoresis.

* * * * *